(12) United States Patent
Houze et al.

(10) Patent No.: US 8,216,606 B2
(45) Date of Patent: *Jul. 10, 2012

(54) DERMAL COMPOSITION FOR CONTROLLING DRUG FLUX COMPRISING TWO ACRYLIC ADHESIVE POLYMERS HAVING DIFFERENT FUNCTIONALITIES AND DIFFERENT SOLUBILITY PARAMETERS

(75) Inventors: David Houze, Coconut Grove, FL (US); Juan Mantelle, Miami, FL (US); David Kanios, Miami, FL (US)

(73) Assignee: Noven Pharmaceuticals, Inc., Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/256,190

(22) Filed: Oct. 24, 2005

(65) Prior Publication Data
US 2006/0240087 A1    Oct. 26, 2006

Related U.S. Application Data

(63) Continuation of application No. 09/768,831, filed on Jan. 24, 2001, now abandoned, which is a continuation of application No. 09/479,966, filed on Jan. 10, 2000, now abandoned.

(60) Provisional application No. 60/115,927, filed on Jan. 14, 1999.

(51) Int. Cl.
*A61F 13/00* (2006.01)
*A61F 13/02* (2006.01)
*A61L 15/16* (2006.01)

(52) U.S. Cl. ...................... 424/449; 424/448

(58) Field of Classification Search .................. 424/449, 424/448
See application file for complete search history.

(56) References Cited

U.S. PATENT DOCUMENTS

| | | | |
|---|---|---|---|
| 4,390,520 A | 6/1983 | Nagai et al. |
| 4,584,355 A | 4/1986 | Blizzard et al. |
| 4,585,836 A | 4/1986 | Homan et al. |
| 4,591,622 A | 5/1986 | Blizzard et al. |
| 4,655,767 A | 4/1987 | Woodard et al. |
| 4,938,759 A | 7/1990 | Enscore et al. |
| 4,994,267 A | 2/1991 | Sablotsky |
| 5,032,207 A | 7/1991 | Sablotsky et al. |
| 5,306,503 A | 4/1994 | Muller et al. |
| 5,405,486 A | 4/1995 | Sablotsky et al. |
| 5,474,783 A | 12/1995 | Miranda et al. |
| 5,656,285 A | 8/1997 | Sablotsky et al. |

(Continued)

FOREIGN PATENT DOCUMENTS

EP    0 827 741    3/1998

(Continued)

OTHER PUBLICATIONS

John Wiley & Sons, Kine, Bejamin et al., "Acrylic and Methacrylic Ester Polymers," pp. 234-299, 1984, *Polymer Science and Engineering*, vol. 1, 2$^{nd}$ Ed.

(Continued)

*Primary Examiner* — Isis Ghali
(74) *Attorney, Agent, or Firm* — Foley & Lardner LLP

(57) ABSTRACT

A dermal composition for administration of a drug comprising a blend of two or more acrylic-based polymers having differing functionalities so as to modulate the drug solubility in the polymer matrix and the delivery rate of the drug, and methods therefor.

24 Claims, 4 Drawing Sheets

U.S. PATENT DOCUMENTS

| | | | |
|---|---|---|---|
| 5,656,286 | A | 8/1997 | Miranda et al. |
| 5,693,335 | A | 12/1997 | Xia et al. |
| 5,725,876 | A | 3/1998 | Mantelle et al. |
| 5,730,999 | A | 3/1998 | Lehmann et al. |
| 5,904,931 | A | 5/1999 | Lipp et al. |
| 5,958,446 | A | 9/1999 | Miranda et al. |
| 6,024,976 | A | 2/2000 | Miranda et al. |
| 6,162,456 | A | 12/2000 | Dunbar et al. |
| 6,221,383 | B1 | 4/2001 | Miranda et al. |
| 6,235,306 | B1 | 5/2001 | Miranda et al. |
| 6,316,022 | B1 | 11/2001 | Mantelle et al. |
| 6,562,363 | B1 | 5/2003 | Mantelle et al. |
| 6,638,528 | B1 | 10/2003 | Kanios |
| 2002/0058058 | A1 | 5/2002 | Mantelle et al. |
| 2005/0169977 | A1 | 8/2005 | Kanios et al. |
| 2006/0078601 | A1 | 4/2006 | Kanios et al. |
| 2006/0078602 | A1 | 4/2006 | Kanios |
| 2006/0078604 | A1 | 4/2006 | Kanios et al. |
| 2006/0233870 | A1 | 10/2006 | Houze et al. |
| 2006/0240087 | A1 | 10/2006 | Houze et al. |

FOREIGN PATENT DOCUMENTS

| | | | |
|---|---|---|---|
| EP | 0 827 741 | A2 | 3/1998 |
| EP | 0 887 075 | | 12/1998 |
| EP | 887075 | A2 * | 12/1998 |
| JP | 61126020 | A * | 6/1986 |
| JP | 04-117323 | A | 4/1992 |
| JP | 09-301854 | A | 11/1997 |
| WO | WO 95/05813 | | 3/1995 |
| WO | WO 95/03193 | | 11/1995 |
| WO | WO 96/06602 | | 3/1996 |
| WO | WO 96/40085 | | 12/1996 |
| WO | WO 00/33812 | A3 | 6/2000 |
| WO | WO 00/51575 | | 9/2000 |
| WO | WO 00/64418 | | 11/2000 |

OTHER PUBLICATIONS

Van Nostrand Reinhold, Satas, Donatas, "Acrylic Adhesives," pp. 396-456, 1989, *Handbook of Pressure-Sensitive Adhesive Technology*, $2^{nd}$ Edition, New York.

Merck & Co., *Merck Index*, $12^{th}$ Edition, pp. THER-1 to THER28; 1969, Rahway, NJ.

U.S. Appl. No. 10/975,749, filed Oct. 28, 2004, Hartwig et al.

Satas, "Acrylic Adhesives," *Handbook of Pressure-Sensitive Adhesive Technology*, $2^{nd}$ ed., D. Satas, ed., pp. 396-456, Van Nostrand Reinhold, New York (1989).

Sobieski et al., "Silicone Pressure Sensitive Adhesives," *Handbook of Pressure-Sensitive Adhesive Technology*. $2^{nd}$, ed., D. Satas, ed., pp. 508-517, Van Nostrand Reinhold, New York (1989).

Office Action issued Oct. 15, 2008, in U.S. Appl. No. 10/975,043.

Office Action issued Jun. 11, 2007, in U.S. Appl. No. 11/256,189.

Office Action issued Mar. 5, 2008, in U.S. Appl. No. 11/256,189.

Office Action issued Mar. 13, 2009, in U.S. Appl. No. 11/256,189.

Office Action issued on Sep. 8, 2009, by the Examiner in U.S. Appl. No. 11/256,189 (US 2006/0233870).

Office Action issued on Nov. 9, 2010 by the Examiner in U.S. Appl. No. 11/256,189 (US 2006/0233870).

Office Action issued on Apr. 14, 2010 by the Examiner in U.S. Appl. No. 11/245,084 (US 2006/0078601).

* cited by examiner

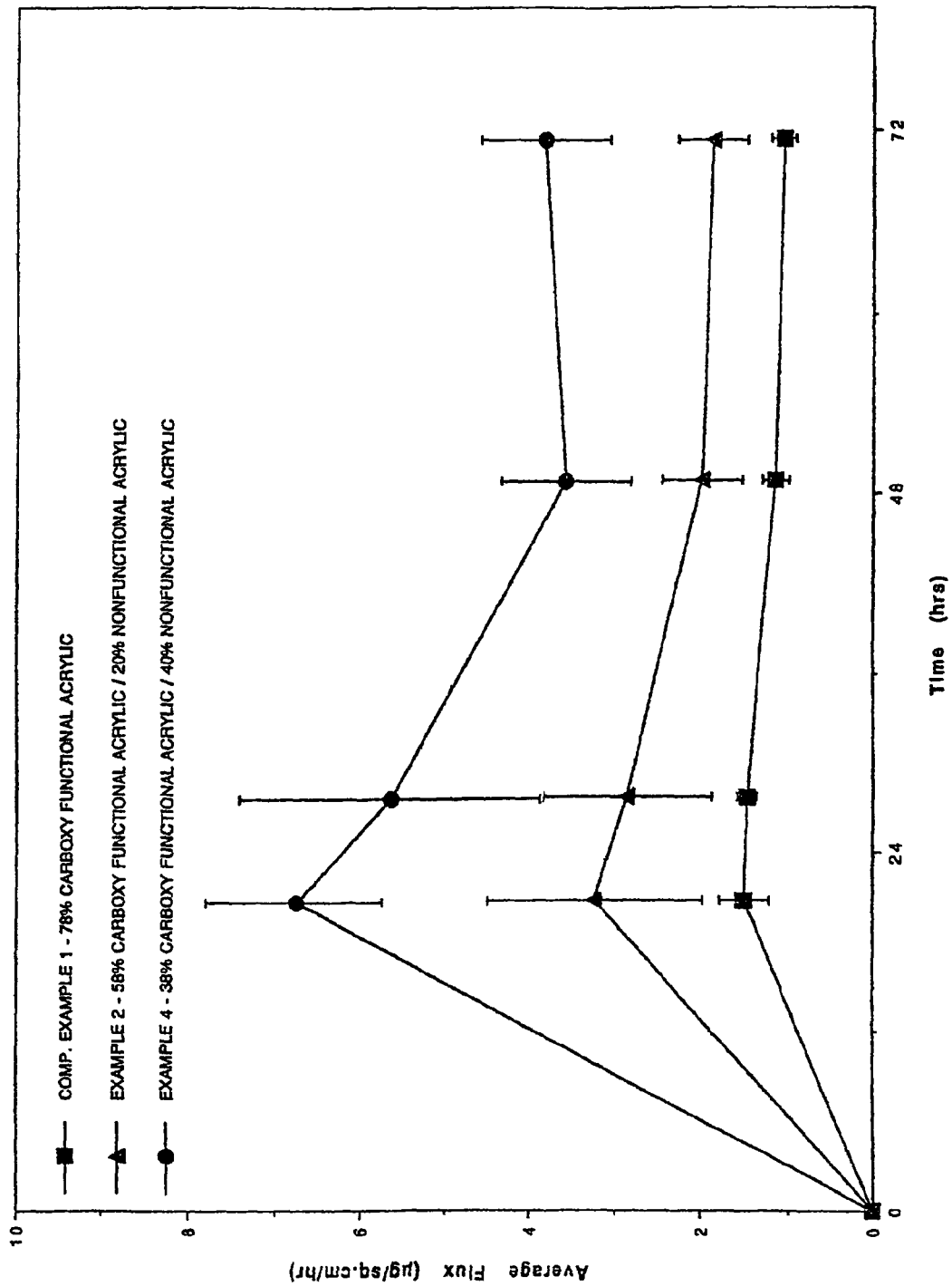

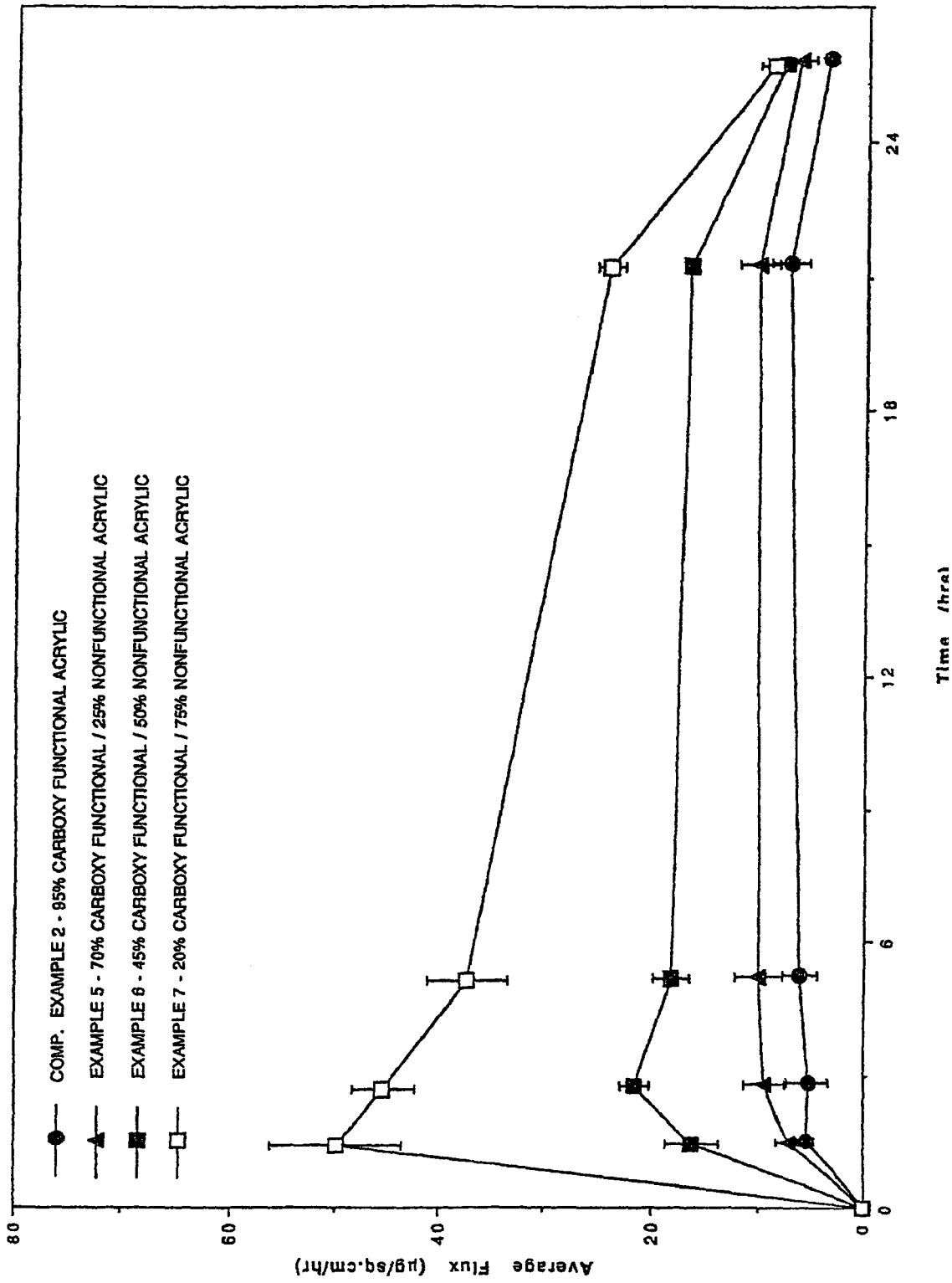

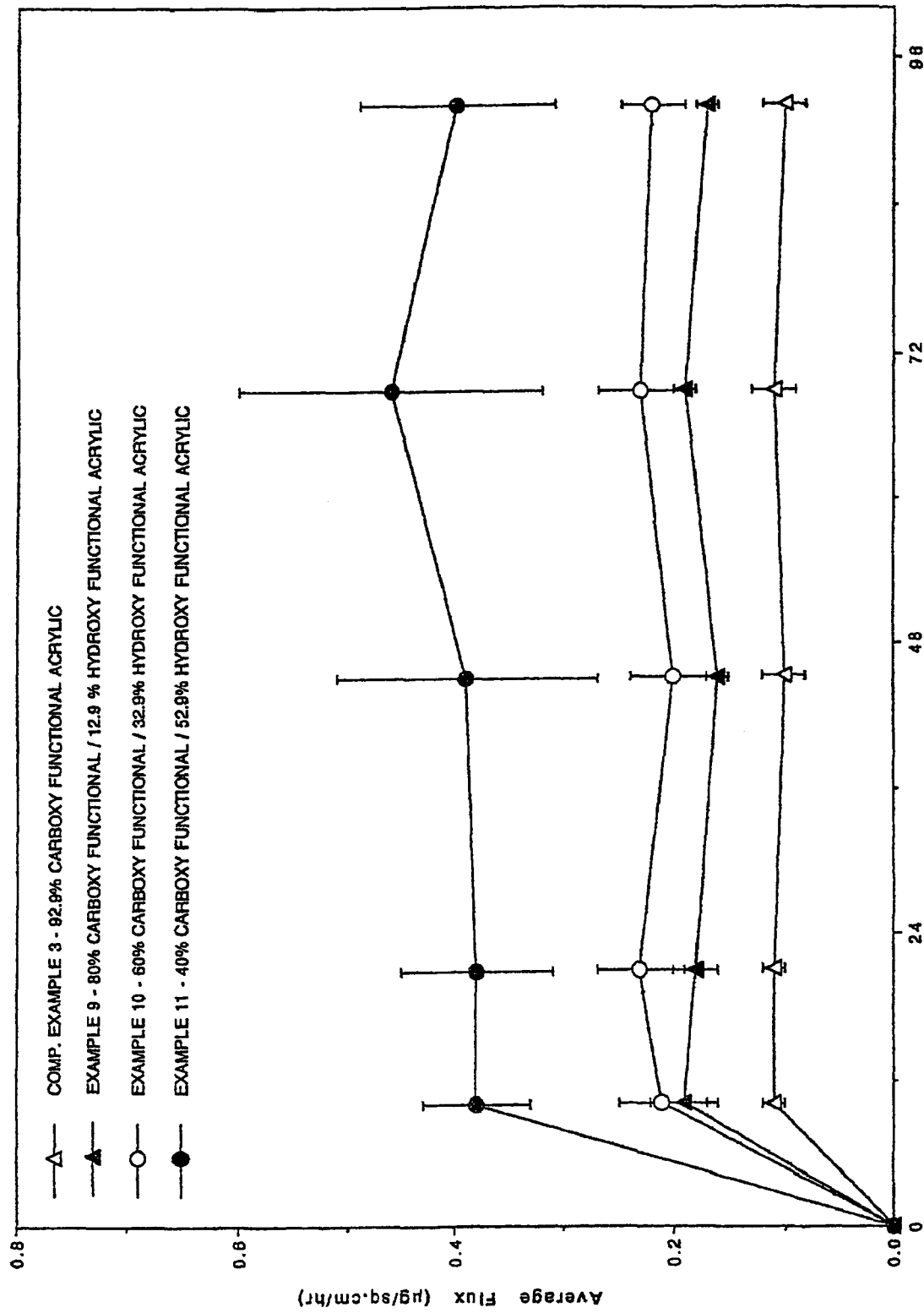

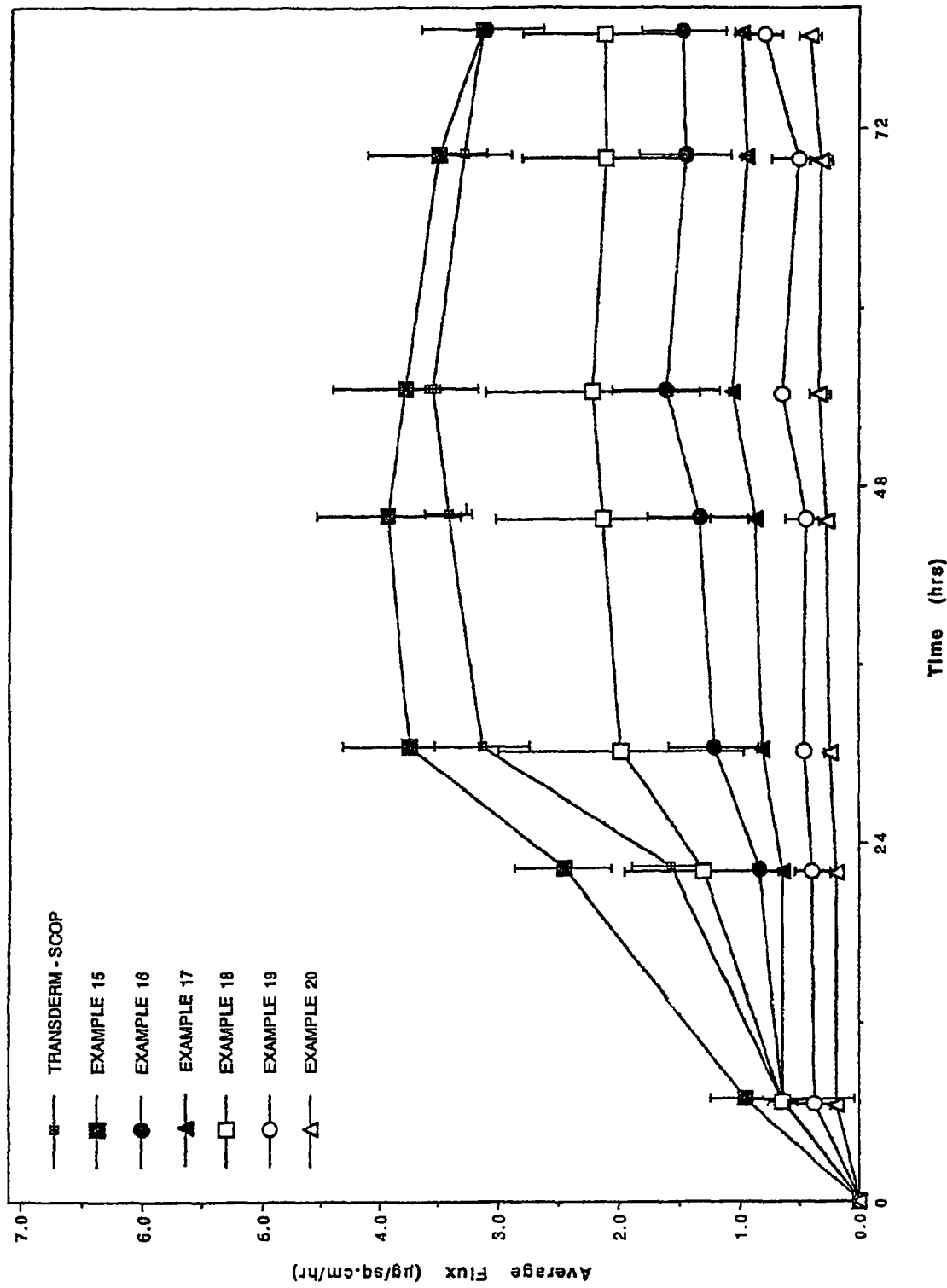

DERMAL COMPOSITION FOR CONTROLLING DRUG FLUX COMPRISING TWO ACRYLIC ADHESIVE POLYMERS HAVING DIFFERENT FUNCTIONALITIES AND DIFFERENT SOLUBILITY PARAMETERS

In accordance with 35 U.S.C. §119 (e), the benefit of provisional application 60/115,927, filed Jan. 14, 1999, is hereby claimed. The entire contents of this provisional application are incorporated herein by reference.

BACKGROUND OF THE INVENTION

1. Field of the Invention

The present invention relates to compositions and methods for dermal administration of drugs, their method of making and method of use. In particular, the present invention is directed to a dermal drug delivery matrix system for the dermal application of one or more drugs, which includes a blend of two acrylic-based polymers having differing functionalities and a therapeutically effective amount of one or more drugs.

2. Description of Related Art

The use of a dermal drug delivery composition, for example a pressure-sensitive adhesive containing a medicament, namely, a drug, as a means for administering therapeutically effective amounts of the medicament is well known. Such known delivery compositions involve incorporation of a medicament into a carrier such as a polymeric and/or a pressure-sensitive adhesive formulation to form a composition of the medicament and a polymer or pressure-sensitive adhesive which also functions as a reservoir for the medicament. If the polymer is a pressure-sensitive adhesive, the pressures-sensitive adhesive also functions to adhere the composition directly to the skin without the requirement for any additional adhesives. The pressure-sensitive adhesive must adhere effectively to the skin and permit migration of the medicament from the carrier to the site of application and/or through the skin and into the bloodstream of the living organism. Many factors influence the design and performance of dermal drug delivery devices, such as desired delivery rate, length of delivery, and the individual drugs themselves. These factors are described in detail in U.S. Pat. No. 5,474,783 (assigned to Noven Pharmaceuticals, Inc., the assignee of the present invention) which is hereby incorporated by reference in its entirety.

Dermal drug delivery compositions based on acrylic pressure-sensitive adhesive polymers are known in the dermal drug delivery art. These acrylic-based polymers are typically used as the pressure-sensitive adhesive by themselves as described in U.S. Pat. No. 4,390,520. They may also be used in combination with other polymers which may or may not be pressure-sensitive adhesive as described in U.S. Pat. No. 4,994,267 (assigned to the assignee of the present application Noven Pharmaceuticals, Inc.). In order to provide for adequate wear properties and drug delivery, acrylic-based pressure-sensitive adhesives are typically polymerized with functional monomers to provide functional groups on the acrylic-based adhesive.

By varying the amount of each type of monomer added, the adhesive and cohesive properties and drug solubility of the resulting polyacrylate can be changed as is known in the art. Typically, the polyacrylate is composed of at least 50% by weight of an acrylate or alkyl acrylate monomer, from 0% to 20% of a functional monomer copolymerizable with the acrylate, and from 0% to 40% of other monomers.

One drawback with the use of acrylic-based polymers with functional groups is that due to the generally high solubility of the drug in the polymer matrix, a large amount of drug generally must be incorporated into the dermal drug delivery composition to saturate it and provide an adequate flux to the skin of the user. Another drawback is that the functional groups provide reaction sites for undesirable degradation reactions of the drug with the polymer matrix.

One way of overcoming the problems of high drug loading and degradation is to physically blend the acrylic-based polymer with another polymer which has a different solubility parameter in order to adjust the solubility and flux of a drug in the blend. In other words, by selectively blending the polymers, a drug delivery system results which can incorporate low concentrations of drug and deliver the same at an adequate and controlled rate, or, alternatively, incorporate high concentrations of drugs while retaining good physical adhesive properties.

A blend of polymers which are particularly suitable are acrylic-based adhesives and polysiloxanes as described in U.S. Pat. No. 5,474,783. While these blends generally provide good results in terms of controlling the flux and the solubility of the drug within the matrix, polysiloxane adhesives are generally more expensive than acrylic-based adhesives resulting in higher production costs. Additionally, the usable range of solubility for silicone-containing blends is significantly lower than is sometimes desired.

SUMMARY OF THE INVENTION

An object of the present invention is to provide a matrix-type polymer dermal drug delivery composition which is simple and inexpensive. Another object of the present invention is to provide an acrylic-based polymer dermal drug delivery composition where the rate of drug delivery from the dermal drug delivery composition may be selectively modulated. Another object of the present invention is to provide a dermal drug delivery composition where the drug loading or drug concentration in the polymer matrix can be selectively controlled. Another object is to provide an acrylic-based dermal drug delivery composition which has a combination of desirable adhesion to mammalian skin in addition to satisfactory drug concentration and flux requirements.

Another object of the present invention is to provide a method for producing a dermal drug delivery composition according to the present invention. Another object of the present invention is to provide a method of modulating drug solubility in a dermal drug delivery composition and drug flux from a polymer matrix.

According to one aspect of the invention, there has been provided a dermal drug delivery composition which includes a blend of: (a) a polymer composition of two or more polymers which includes: (i) a first acrylic-based polymer having a first functionality and solubility parameter; and (ii) a second acrylic-based polymer having a second functionality and solubility parameter, wherein the first and second functionalities differ in the amount and type of functional groups to provide an acrylic-based polymer combination having a net functionality proportional to the ratio of the first and second acrylic-based polymers used, and are present in proportions to provide a net solubility parameter; and (b) a therapeutically effective amount of one or more drugs incorporated into the polymer composition.

According to another aspect of the invention, there has been provided a method of producing a dermal composition, comprising the steps of: (1) producing a blend of: (a) a polymer composition of two or more polymers which includes: (i)

a first acrylic-based polymer having a first functionality and solubility parameter; and (ii) a second acrylic-based polymer having a second functionality and solubility parameter, wherein the first and second functionalities differ in the amount and type of functional groups to provide an acrylic-based polymer combination having a net functionality proportional to the ratio of the first and second acrylic-based polymers used, and are blended in proportions to provide a net solubility parameter; and (b) a therapeutically effective amount of one or more drugs incorporated into the polymer composition; (2) forming the blend into a polymer matrix; and (3) drying the polymer matrix to remove the solvent system to form the dermal composition.

According to still another aspect of the invention, there has been provided a method of controlling the flux of a drug from a dermal drug delivery composition, comprising the steps of: (a)

selecting at least two polymers which includes: (i) a first acrylic-based polymer having a first functionality and solubility parameter; and (ii) a second acrylic-based polymer having a second functionality and solubility parameter, wherein the first and second functionalities differ in the amount and type of functional groups to provide a polymer combination having a net solubility of one or more drugs within the composition proportional to the ratio of the first and second acrylic-based polymers used; (b) combining the at least two acrylic-based polymers with a therapeutically effective amount of one or more drugs to form the dermal drug delivery composition, wherein the one or more drugs have a flux which is determined by the net solubility in the composition and is different than the flux of a composition produced solely from the first or second acrylic-based polymers alone.

These and other objects will be readily apparent to those skilled in the art from the detailed description of preferred embodiments which follows.

BRIEF DESCRIPTION OF THE DRAWINGS

FIG. 1 is a graphic representation of the average flux of haloperidol versus time with different proportions of acid functional and non-functional acrylic-based polymers.

FIG. 2 is a graphic representation of the average flux of nicotine versus time with different proportions of acid functional and non-functional acrylic-based polymers.

FIG. 3 is a graphic representation of the average flux of clonidine versus time with different proportions of acid functional and hydroxy functional acrylic-based polymers.

FIG. 4 is a graphic representation of the average flux of scopolamine versus time with different proportions of acid functional and non-functional acrylic-based polymers.

DETAILED DESCRIPTION OF THE PREFERRED EMBODIMENTS

As used herein, the term "dermal" refers to delivery, administration or application of a drug by means of direct contact with tissue, such as skin or mucosa. Such delivery, administration or application is also known as percutaneous, transdermal, transmucosal and buccal. Similarly, "skin" is meant to include mucosa which further includes oral, buccal, nasal, rectal and vaginal mucosa.

As used herein, a "dermal composition" is defined as a composition which contains one or more drugs therein. The dermal composition is applied to a dermal area, described above for dermal administration or application of the one more drugs. The dermal composition includes a polymer matrix with the one or more drugs contained therein. As described below, in a preferred embodiment, the polymer matrix may be a pressure-sensitive adhesive for direct attachment to a user's skin. Alternatively, the polymer matrix may be non-adhesive with separate adhesion means for adhering the composition to the user's skin.

As used herein, the terms "blend" and "mixture" are used herein to mean that there is no, or substantially no, chemical reaction or crosslinking (other than simple H-bonding) between the different polymers in the polymer matrix. However, crosslinking between a single polymer component is fully contemplated to be within the scope of the present invention.

As used herein, the term "pressure-sensitive adhesive" refers to a viscoelastic material which adheres instantaneously to most substrates with the application of very slight pressure and remains permanently tacky. A polymer or dermal composition is a pressure-sensitive adhesive within the meaning of the term as used herein if it has the adhesive properties of a pressure-sensitive adhesive per se or functions as a pressure-sensitive adhesive by admixture with tackifiers, plasticizer or other additives.

As used herein, a "polymer composition of two or more polymers" is defined as a physical blend of at least two polymers and can include 3 or more polymers. The two or more polymers includes the acrylic-based polymers described herein and can optionally include other polymers discussed more fully below.

As used herein, "acrylic-based" polymer is defined as any polyacrylate, polyacrylic, acrylate and acrylic polymer. The acrylic-based polymers can be any of the homopolymers, copolymers, terpolymers, and the like of various acrylic acids or esters. The acrylic-based polymers useful in practicing the invention are polymers of one or more monomers of acrylic acids and other copolymerizable monomers. The acrylic-based polymers also include copolymers of alkyl acrylates and/or methacrylates and/or copolymerizable secondary monomers. Acrylic-based polymers with functional groups as described more fully below, are copolymerized with functional monomers.

As used herein, "functional monomers or groups," are monomer units in an acrylic-based polymers which have reactive chemical groups which modify the acrylic-based polymers directly or provide sites for further reactions. Examples of functional groups include carboxyl, epoxy and hydroxy groups.

As used herein, "functionality" is broadly defined as a measure of the type and quantity of functional groups that a particular acrylic-based polymer has. This definition also encompasses acrylic-based polymers having no or substantially no functional groups.

As used herein "non-functional acrylic" is defined as an acrylic-based polymer which has no or substantially no functional reactive moieties present in the acrylic. These are generally acrylic esters which can be copolymerized with other monomers which do not have functional groups, such as vinyl acetate.

As used herein "flux" is defined as the percutaneous absorption of drugs through the skin, and is described by Fick's first law of diffusion:

$$J = -D(dC_m/dx),$$

where J is the flux in g/cm$^2$/sec, D is the diffusion coefficient of the drug through the skin in cm$^2$/sec and $dC_m/dx$ is the concentration gradient of the active agent across the skin.

As used herein, "matrix" is defined as a polymer composition which incorporates a therapeutically effective amount of the drug therein. The matrix may be monolithic as described below, or it may use separate attachment means for holding it to the user's skin. A dermal drug delivery system with a matrix may optionally include additional drug supply means for continuously replenishing the drug supply in the matrix.

As used herein "monolithic" is defined as a matrix device which is adhesive, pressure-sensitive or otherwise.

As used herein, the term "drug" (and its equivalents, "active agent," "bioactive agent," "medicament" and "pharmaceutical or any other similar term) is intended to have the broadest meaning and includes any chemical or biological material or compound which induces at least one of any therapeutic, prophylactic, pharmacological, physiological, aesthetic, cosmetic, or any other desired, usually beneficial, effect, localized or systemic, to a living organism. It should be noted that the drugs may be used singularly or in mixtures of two or more drugs, and in amounts sufficient to prevent, cure, diagnose, mitigate or treat a disease or condition, as the case may be.

As used herein, when drug is used in a "therapeutically effective amount" means that the concentration of the drug in the dermal drug delivery composition results in a therapeutic level of the drug being delivered to the site of application or through the skin and into the bloodstream over the period of time that the dermal composition is to be used, preferably with zero order kinetics. Such delivery is dependent on a great number of variables including the drug, the time period for which the individual dosage unit is to be used, the flux rate of the drug from the system and a number of other variables. The amount of drug needed can be experimentally determined based on the flux rate of the drug through the system and through the skin when used with or without enhancers. Having determined the flux rate needed, the dermal delivery system is designed so that the release rate over the period of time of therapeutic use will be at least equal to the flux rate. Of course, the surface area of the dermal delivery system also affects the delivery of the drug from the system through the skin.

The present invention is based on the discovery that a polymer matrix dermal drug delivery composition having good adhesion properties, controllable drug solubility and flux can be achieved by physically blending two acrylic-based polymers which have different functionalities. The functionality of one of the acrylic-based polymers is such that it has a high drug solubility or loading requirements. The functionality of the other acrylic-based polymer is such that a drug has a lower solubility which accordingly requires a relatively low drug loading to produce a flux which is substantially equivalent to the more highly loaded polymer.

The combination of these two acrylic-based polymers results in a dermal drug delivery composition having a characteristic "net solubility parameter." The net solubility parameter can be adjusted by the kinds and proportions of the acrylic-based polymers. This provides a selectable modulation of the delivery rate of the drug by adjusting the solubility of the drug in the acrylic-based polymer composition.

Solubility parameter has been defined as the sum of all intermolecular attractive forces, which are empirically related to the extent of mutual solubility of many chemical species. An in-depth discussion of solubility parameter can be found in U.S. Pat. No. 5,474,783. In other words, the solubility parameter determines how much of a drug can be incorporated into a polymer matrix before the polymer matrix becomes saturated with the drug.

Another factor to be considered in formulating the dermal composition is that if the dermal composition is adhesive at room temperature according to a preferred embodiment, then the composition should have good adherence to skin, the ability to be peeled or otherwise removed without substantial trauma to the skin, retention of tack, etc. In other words, the dermal drug delivery must have sufficient wear properties. In general, the dermal polymer drug delivery composition should have a glass transition temperature ($T_g$), measured using a differential scanning calorimeter, of between about −70° C. to 0° C. Since dermal drug delivery compositions made with high proportions of non-functional acrylic-based polymers generally do not have sufficient wear properties, there is an upper limit on the amount of non-functional acrylic-based adhesive incorporated into the composition. This upper limit generally depends on the drug being loaded into the composition, the drug loading amounts, other additives such as enhancers, and the type of the other acrylic-based adhesive used. The upper limit can be determined by routine experimentation using the present specification as a guide.

Non-functional acrylic-based polymers can include any acrylic based polymer having no or substantially no free functional groups. The acrylic based polymer can include homopolymers, copolymers and terpolymers. The monomers used to produce the polymers can include alkyl acrylic or methacrylic esters such as methyl acrylate, ethyl acrylate, propyl acrylate, amyl acrylate, butyl acrylate, 2-ethylbutyl acrylate, hexyl acrylate, heptyl acrylate, octyl acrylate, nonyl acrylate, 2-ethylhexyl acrylate, decyl acrylate, dodecyl acrylate, tridecyl acrylate and the corresponding methacrylic esters.

Acrylic-based polymers having functional groups are copolymers or terpolymers which contain in addition to the nonfunctional monomer units described above, further monomer units having free functional groups. The monomers can be monofunctional or polyfunctional. These functional groups include carboxyl groups, hydroxy groups, amino groups, amido groups, epoxy groups, etc. Preferred functional groups are carboxyl groups and hydroxy groups. Preferred carboxyl functional monomers include acrylic acid, methacrylic acid, itaconic acid, maleic acid, and crotonic acid. Preferred hydroxy functional monomers include 2-hydroxyethyl methacrylate, 2-hydroxyethyl acrylate, hydroxymethyl acrylate, hydroxymethyl methacrylate, hydroxyethyl acrylate, hydroxyethyl methacrylate, hydroxypropyl acrylate, hydroxypropyl methacrylate, hydroxybutyl acrylate, hydroxybutyl methacrylate, hydroxyamyl acrylate, hydroxyamyl methacrylate, hydroxyhexyl acrylate, hydroxyhexyl methacrylate.

These functional monomers are incorporated into the copolymer or terpolymer in an amount of 0.1 to 20% by weight, preferably 0.1 to 12% by weight, more preferably 0.1 to 8% by weight and still more preferably 4 to 8% by weight based on the dry weight of the total acrylic-based polymer.

Both the acrylic-based polymer having substantially no functional groups and acrylic-based polymers having functional groups can optionally include further modifying monomers. These modifying monomers can include any conceivable monomer that is capable of undergoing vinyl polymerization. For example, the incorporation of styrene monomers can be used to increase the glass transition temperature and are sometimes used to improve the cohesive strength. The copolymerization of vinyl acetate monomers with acrylic esters are also used to form acrylic-based polymers. Ethylene can also be copolymerized with acrylic esters and vinyl acetate to give suitable acrylic-based polymers.

In a particularly preferred embodiment, the dermal composition is a pressure-sensitive adhesive. More preferably, the adhesive properties of the dermal composition are provided by one or both of the acrylic-based polymers being pressure-sensitive adhesive.

Further details and examples of acrylic-based adhesives, functional monomers, and polymers which have no functional groups and which are suitable in the practice of the invention are described in Satas, "Acrylic Adhesives," *Handbook of Pressure-Sensitive Adhesive Technology, 2nd ed.*, pp. 396-456 (D. Satas, ed.), Van Nostrand Reinhold, New York (1989); "Acrylic and Methacrylic Ester Polymers," *Polymer Science and Engineering*, Vol. 1, 2nd ed., pp 234-268, John Wiley & Sons, (1984); U.S. Pat. No. 4,390,520; and U.S. Pat. No. 4,994,267 all of which are expressly incorporated by reference in their entireties.

Preferred acrylic-based adhesives which are commercially available include the acrylic-based adhesives sold under the trademarks Duro-Tak 87-2287 (a non-crosslinked vinyl acetate acrylic pressure-sensitive adhesive with hydroxy functionality), Duro-Tak 87-4098 (a non-functional, non-crosslinked acrylic pressure sensitive adhesive), Duro-Tak 87-2852 (a crosslinked acrylic-based pressure-sensitive adhesive with carboxyl functionality), Duro-Tak 87-2196 (carboxy functional, crosslinked), Duro-Tak 87-2296 (carboxy functional, crosslinked), Duro-Tak 87-2194 (carboxy functional, crosslinked), Duro-Tak 87-2516 (hydroxy functional, crosslinked), Duro-Tak 87-2070 (carboxy and hydroxy functional, crosslinked), Duro-Tak 87-2353 (carboxy functional, non-crosslinked), Duro-Tak 87-2154 (carboxy functional, crosslinked), and Duro-Tek 87-2510 (non-functional non-crosslinked), and are all sold by National Starch and Chemical Corporation, Bridgewater, N.J. Other suitable acrylic-based pressure-sensitive adhesive include HRJ 4483, 10127, and 11588 (non-functional acrylic-based pressure-sensitive adhesives) sold by Schenectady International, Inc., Schenectady, N.Y. Other suitable acrylic-based adhesives are those sold under the trademarks Gelva-Multipolymer Solution GMS 2480, Gelva 788, Gelva 737, Gelva 263, Gelva 1430, Gelva 1753, Gelva 1151, Gelva 2450, and Gelva 2495 all sold by Monsanto; St. Louis, Mo.

The types of acrylic-based polymers having different functionalities and their proportions in the dermal drug delivery composition can vary broadly and generally depends on the solubility of the particular drug being incorporated into the polymer matrix, the required flux and the amount of time the composition will be required to deliver a therapeutically effective amount of the drug to the user's skin.

The proportion of the two acrylic-based polymers can be adjusted to either increase or decrease the saturation concentration or drug loading of the drug in the composition, and can also be used to modulate the shape of the flux curve. For example, the saturation concentration of a drug in a first functional acrylic-based polymer can be lowered by blending in a non-functional acrylic-based polymer or another acrylic-based polymer which has either a lower proportion or different functional groups.

Alternatively, the saturation concentration in a first functional acrylic-based polymer can be lowered by blending another functional acrylic-based polymer which has a functional group which does not have as great of an affinity for the drug as the functional group in the first functional acrylic-based polymer, which results in a lower solubility. This combination of acrylics is typically used when a non-functional acrylic-based pressure-sensitive polymer has too great a propensity to solubilize the drug.

This combination of a non-functional or lower solubility functional acrylic-based polymer with a functional acrylic-based polymer, creates a greater thermodynamic driving force and greater flux of drug from the composition. As noted above, in the case of the preferred embodiment where the dermal composition is a pressure-sensitive adhesive, there is an adhesion limit to the amount of non-functional acrylic-based polymer that can be incorporated into the composition.

Conversely, the saturation concentration of a drug can be increased by increasing the proportion of the functional acrylic-based polymer incorporated into the composition. This creates a greater drug loading capacity or a decreased flux which, depending on the application, is sometimes desirable.

Exact proportions of acrylic-based polymers used are generally dependant on the specific drug, its desired delivery rate and the duration of drug delivery. Those skilled in the art can readily determine the rate of delivery of the drug from the dermal drug delivery composition in order to select suitable combination of the acrylic-based polymers and drug for a particular application. Various techniques can be used to determine the rate of delivery of the drug from the polymer. Illustratively, the rate of delivery can be determined by measuring the transfer of drug from one chamber to another through cadaver skin over time, and calculating from the obtained data, the drug delivery or flux rate.

The proportions of acrylic-based polymers also depend on the content of the functional monomer units in the functional acrylic. For example, a dermal composition will require less of a functional acrylic that contains 20% by weight of functional groups as opposed to one that contains 0.5% by weight of functional groups to achieve the same effect required for solubility and flux. Broadly speaking, the amount of functional acrylic is generally within the range of about 1 to 99 weight % and preferably 5 to 95 weight %, more preferably 20 to 75 weight %, even more preferably 30 to 65 weight %, based on the total polymer content of the dermal composition. The amount of non-functional acrylic or acrylic with a functional group which does not have as great of an affinity for the drug, is within the range of about 99 to 1 weight %, preferably 95 to 5 weight %, more preferably 75 to 20 weight % and even more preferably 30 to 65 weight %, based on the total polymer content of the dermal composition.

Other natural or synthetic polymers, which may or may not be adhesives, can also be included in the dermal composition according to the present invention. For example, polyvinylpyrrolidone ("PVP") can be included to increase the maximum concentration of the drug in the composition. The use of PVP in a dermal composition is fully described in U.S. Pat. No. 5,656,286 which is expressly incorporated in its entirety. Other suitable polymers and pressure-sensitive adhesives include polysiloxanes and rubbers. The addition of such other polymers to a dermal composition is fully described in U.S. Pat. No. 5,474,783 which is incorporated herein in its entirety.

The drugs used in the present invention can include a single drug or mixtures of one or more drugs. Any drug suitable for dermal administration by methods previously known in the art and by the methods of the present invention can be used in the present invention, and further include such active agents that may be later established as drugs and are suitable for delivery by the present invention. These drugs include those categories and species of drugs set forth on page ther-1 to ther-28 of the *Merck Index,* 12th Edition Merck and Co. Rahway, N.J. (19969). This reference is incorporated by reference in its entirety. Exemplary of drugs that can be administered by the novel dermal drug delivery system include, but are not limited to:

1. α-Adrenergic agonist agents such as Phenylpropanolamine.

2. Analgesics and/or Anti-Migraine such as Acetaminophen, Acetylsalicylic Acid, Buprenorphine, Codeine, Fentanyl, Lisuride, Salicylic Acid derivatives and Sumatriptan.

3. Androgen agents such as Fluoxymesterone, Methyl Testosterone, Oxymesterone, Oxymetholone, Testosterone and Testosterone derivatives.

4. Anesthetic agents such as Benzocaine, Bupivicaine, Cocaine, Dibucaine, Dyclonine, Etidocaine, Lidocaine, Mepivacaine, Prilocaine, Procaine and Tetracaine.

5. Anoretic agents such as Fenfluramine, Mazindol and Phentermine.

6. Anti-Bacterial (antibiotic) agents including Aminoglycosides, β-Lactams, Cephamycins, Macrolides, Penicillins, Polypeptides and Tetracyclines.

7. Anti-Cancer agents such as Aminolevulinic Acid and Tamoxifen.

8. Anti-Cholinergic agents such as Atropine, Eucatropine and Scopolamine.

9. Anti-Diabetic agents such as Glipizide, Glyburide, Glypinamide and Insulins.

10. Anti-Fungal agents such as Clortrimazole, Ketoconazole, Miconazole, Nystatin and Triacetin.

11. Anti-Inflammatory and/or Corticoid agents such as Beclomethasone, Betamethasone, Betamethasone Diproprionate, Betamethasone Valerate, Corticosterone, Cortisone, Deoxycortocosterone and Deoxycortocosterone Acetate, Diclofenac, Fenoprofen, Flucinolone, Fludrocortisone, Fluocinonide, Fluradrenolide, Flurbiprofen, Halcinonide, Hydrocortisone, Ibuprofen, Ibuproxam, Indoprofen, Ketoprofen, Ketorolac, Naproxen, Oxametacine, Oxyphenbutazone, Piroxicam, Prednisolone, Prednisone, Suprofen and Triamcinolone Acetonide.

12. Anti-Malarial agents such as Pyrimethamine.

13. Anti-Parkinson's and/or Anti-Alzhiemer's agents such as Bromocriptine, 1-Hydroxy-Tacrine, Levodopa, Lisaride Pergolide, Pramipexole, Ropinirole, Physostigimine, Selegiline (Deprenyl and L-Deprenyl), Tacrine Hydrochloride and Teruride.

14. Anti-Psychotic and/or Anti-Anxiety agents such as Acetophenazine, Azapirones, Bromperidol, Chlorproethazine, Chlorpromazine, Fluoxetine, Fluphenazine, Haloperidol, Loxapine, Mesoridazine, Molindone, Ondansetron, Perphenazine, Piperacetazine, Thiopropazate, Thioridazine, Thiothixene, Trifluoperazine and Triflupromazine.

15. Anti-Ulcerative agents such as Enprostil and Misoprostol.

16. Anti-Viral agents such as Acyclovir, Rimantadine and Vidarabine.

17. Anxiolytic agents such as Buspirone, Benzodiazepines such as Alprazolam, Chlordiazepoxide, Clonazepam, Clorazepate, Diazepam, Flurazepam, Halazepam, Lorazepam, Oxazepam, Oxazolam, Prazepam and Triazolam.

18. β-Adrenergic agonist agents such as Albuterol, Carbuterol, Fenoterol, Metaproterenol, Rimiterol, Quinterenol, Salmefamol, Soterenol, Tratoquinol, Terbutaline and Terbuterol.

19. Bronchodilators such as Ephedrine derivatives including Epiniphrine and Isoproterenol, and Theophylline.

20. Cardioactive agents such as Atenolol, Benzydroflumethiazide, Bendroflumethiazide, Calcitonin, Captopril, Chlorothiazide, Clonidine, Dobutamine, Dopamine, Diltiazem, Enalapril, Enalaprilat, Gallopamil, Indomethacin, Isosorbide Dinitrate and Mononitrate, Nicardipine, Nifedipine, Nitroglycerin, Papaverine, Prazosin, Procainamide, Propranolol, Prostaglandin $E_1$, Quinidine Sulfate, Timolol, and Verapamil.

21. Central nervous system stimulants and agents such as Dextroamphetamine, Methylphenidate and Nicotine.

22. Cholinergic agents such as Acetylcholine, Arecoline, Bethanechol, Carbachol, Choline, Methacoline, Muscarine and Pilocarpine.

23. Estrogens such as Conjugated Estrogenic Hormones, Equilenin, Equilin, Esterified Estrogens, 17β-Estradiol, Estradiol Benzoate, 17β-Estradiol Valerate, Estradiol 17β-Cypionate, Estriol, Estrone, Estropipate, 17β-Ethinyl Estradiol and Mestranol.

24. Muscle relaxants such as Baclofen.

25. Narcotic antagonist agents such Nalmfene and Naloxone.

26. Progestational agents such as Chlormadinone and Chlormadinone Acetate, Demegestone, Desogestrel, Dimethisterone, Dydrogesterone, Ethinylestrenol, Ethisterone, Ethynodiol and Ethynodiol Diacetate, Gestodene, 17α-Hydroxyprogesterone, Hydroxygesterone Caproate, Medroxyprogesterone and Medroxyprogesterone Acetate, Megestrol Acetate, Melengestrol, Norethindrone and Norethidrone Acetate, Norethynodrel, Norgesterone, Norgestrel, 19-Norprogesterone, Progesterone, Promegestone and esters thereof.

Particularly preferred drugs include alprazolam, captopril, clonidine, clonaazepam, enalapril, fluoxetine, haloperidol, ketoprofen, loratadine, methimazole (anti-hyperthyroid), methylphenidate, methyl testosterone, nicotine, nitroglycerin, pramipexole, ropinirole, selegiline (deprenyl and L-deprenyl), scopolamine and testosterone.

The drugs and mixtures thereof can be present in the composition in different forms, depending on which yields the optimum delivery characteristics. Thus, the drug can be in its free base form or in the form of salts, esters, or any other pharmacologically acceptable derivatives, or as prodrugs, components of molecular complexes or as combinations of these. Free base forms of drugs which have a greater affinity for the acid (carboxyl) functional group in a carboxyl functional acrylic-based polymer are preferred in some applications.

As noted above, with the present invention a greater flux of the drug(s) can be achieved with the same loading of the drug(s) into the dermal drug delivery composition. Put in a slightly different way, using a lower loading or concentration of the drug in the dermal drug delivery composition according to the present invention will result in a comparable flux to conventional acrylic-based dermal drug delivery compositions. The concentration of the drug incorporated in the dermal drug delivery composition varies depending on the drug, the composition of the acrylic-based polymers, the required flux or desired therapeutic effect and the duration for which the dermal drug delivery composition is to provide therapy.

For most drugs, the passage of the drugs through the skin or mucosa will be the rate-limiting step in delivery. Thus, the amount of drug and the rate of release is typically selected so as to provide delivery characterized by a pseudo-zero order time dependency for a prolonged period of time. The minimum amount of drug in the system is selected based on the amount of drug which passes through the skin or mucosa in the time span for which the device is to provide therapy. Normally, the amount of drug in the system can vary from about 0.1 to 40% by weight, preferably 0.5 to 20% by weight, and optimally 1-10% by weight, based on the total dry weight of the dermal composition.

The dermal drug delivery composition can also contain one or more agents known to accelerate the delivery of the drug through the skin or mucosa. These agents have been referred to as penetration enhancers, accelerants, adjuvants, and absorption promoters, and are collectively referred to as "enhancers."

Some examples of enhancers are monohydric alcohols such as ethanol and isopropyl, butyl and benzyl alcohols, or dihydric alcohols such as ethylene glycol, diethylene glycol, or propylene glycol, dipropylene glycol and trimethylene glycol, or polyhydric alcohols such as glycerin, sorbitol and polyethylene glycol, which enhance drug solubility; polyethylene glycol ethers of aliphatic alcohols (such as cetyl, lauryl, oleyl and stearyl) including polyoxyethylene (4) lauryl ether, polyoxyethylene (2) oleyl ether and polyoxyethylene (10) oleyl ether commercially available under the trademark BRIJ® 30, 93 and 97, respectively, from ICI Americas, Inc., and others such as BRIJ® 35, 52, 56, 58, 72, 76, 78, 92, 96, 700 and 721; vegetable, animal and fish fats and oils such as olive and castor oils, squalene, and lanolin; fatty acids such as oleic, linoleic, and capric acid; fatty acid esters such as propyl oleate, decyl oleate, isopropyl palmitate, glycol palmitate, glycol laurate, dodecyl myristate, isopropyl myristate and glycol stearate which enhance drug diffusibility; fatty acid alcohols such as oleyl alcohol and its derivatives; fatty acid amides such as oleamide and its derivatives; urea and urea derivatives such as allantoin which affect the ability of keratin to retain moisture; polar solvents such as dimethyldecylphosphoxide, methyloctylsulfoxide, dimethyllaurylamide, dodecylpyrrolidone, isosorbitol, dimethylacetonide, dimethylsulfoxide, decylmethylsulfoxide and dimethylformamide which affect keratin permeability; salicylic acid which softens the keratin; amino acids which are penetration assistants; benzyl nicotinate which is a hair follicle opener; and higher molecular weight aliphatic surfactants such as lauryl sulfate salts which change the surface state of the skin; and esters of sorbitol and sorbitol anhydride such as polysorbate 20 commercially available under the trademark Tween® 20 from ICI Americas, Inc., as well as other polysorbates such as 21, 40, 60, 61, 65, 80, 81, and 85. Other enhancers include enzymes, ascorbic acid, panthenol, butylated hydroxytoluene, tocopherol, tocopherol acetate, tocopheryl linoleate.

The dermal compositions of the present invention may also contain one or more solvents or co-solvents. Such solvents and co-solvents are those known in the art, and are non-toxic, pharmaceutically acceptable substances, preferably liquids, which do not substantially negatively affect the properties of the polymer composition or solubility of the active agents at the concentrations used. The solvent and co-solvent can be for the active agent or for the polymers composition, or both. The solvent is preferably a polyhydric alcohol or combination of polyhydric alcohols.

The term "polyhydric alcohol" means any organic polyalcohol and includes dipropylene glycol, propylene glycol, polyethylene glycol, glycerin, butylene glycol, hexylene glycol, polyoxyethylenes, polypropylene glycol, sorbitol, ethylene glycol, and the like. Other suitable solvents include fatty acids such as oleic acid, linoleic acid, capric acid and the like; polyethylene, polypropylene and ethers of fatty acids, as well as fatty esters, for example isopropyl myristate, or fatty alcohols. Further suitable solvents include vegetable, animal and fish oils such as castor oil, canola oil, safflower oil, cod liver oil, and lanolin, mineral oil, lecithin, tocopherol and tocopheryl acetate, and other non-toxic, non-volatile solvents commonly used in transdermal or transmucosal compositions.

The above-mentioned polyhydric alcohols may include those having 2 to 6 alcoholic hydroxyl groups. Such polyhydric alcohols include glycols, triols and polyols having 4 to 6 alcoholic hydroxyl groups. Typical of said glycols are glycols containing 2 to 6 carbon atoms, e.g. ethylene glycol, propylene glycol, butylene glycol, polyethylene glycol (average molecular weight about 200-8,000, preferably about 200 to 6,000), etc. Examples of said triols include glycerin, trimethylolpropane, etc. Said polyols are exemplified by sorbitol (sorbit), polyvinylpyrrolidone, etc. These polyhydric alcohols may be used either singularly or in combination (preferably, of two or three). Thus, for example, glycerin or dipropylene glycol alone, or a mixture of either glycerin or dipropylene glycol with butylene glycol, can be employed.

Among those polyhydric alcohols, those which are low in volatility such as dipropylene glycol, glycerin propylene glycol, butylene glycol, and sorbitol are generally preferred.

Although the exact amount of the polyhdric alcohols, or fatty acids, esters, ethers or alcohols, that may be used in the dermal composition depends on the nature and amount of other components, and therefore cannot be stated in general terms, the proportion may range up to about 30% by weight, and preferably from about 3% to about 15% by weight, and more preferably from about 5% to about 10% by weight based on the dry weight of the dermal composition.

Some drugs, for example nitroglycerin, nicotine and selegiline, function as plasticizers in the polymer matrix because they are readily soluble to a certain degree in the polymers comprising the matrix. For drugs which are not readily soluble, or for which a saturation or super-saturation of the drug is desired, a co-solvent can be added. As used herein, "co-solvents" are defined to include solvents and other agents which increase the solubility of a drug in the polymer matrix. Co-solvents include lecithin, retinol derivatives, tocopherol, dipropylene glycol, triacetin, propylene glycol, saturated and unsaturated fatty acids, mineral oil, silicone fluid, alcohols, butyl benzyl phthalate, butylene glycol, glycerin and the like. The co-solvents are present in an amount up to about 30% by weight, more preferably from about 2% to about 15% and more preferably from about 3% to about 10% by weight, based on the dry weight of the dermal composition.

In addition to the above ingredients, there may also be incorporated various pharmaceutically acceptable additives and excipients available to those skilled in the art. These additives include tackifying agents, such as aliphatic hydrocarbons, mixed aliphatic and aromatic hydrocarbons, aromatic hydrocarbons, substituted aromatic hydrocarbons, hydrogenated esters, polyterpenes and hydrogenated wood rosins. Additional additives include binders such as lecithin which "binds" the other ingredients, or Theological agents (thickeners) containing silicone such as fumed silica, reagent grade sand, precipitated silica, amorphous silica, colloidal silicon dioxide, fused silica, silica gel, quartz and particulate siliceous materials commercially available as Syloid®, Cabosil®, Aerosil®, and Whitelite®, for purposes of enhancing the uniform consistency or continuous phase of the final composition. Other additives and excipients include diluents, stabilizers, fillers, clays, buffering agents, crosslinking agents, biocides, humectants, anti-irritants, antioxidants, preservatives, flavoring agents, colorants, pigments and the like. Such additives or excipients are typically used in amounts up to 25% by weight, and preferably from about 0.1% to about 10% by weight based on the drug weight of the dermal composition.

The dermal compositions according to the present invention can be prepared by mixing the two or more polymers, in powder or liquid form, with the active agent, with or without the other ingredients. When a pressure-sensitive adhesive is used, a volatile, lower molecular weight solvent, for example an organic solvent, is typically supplied with the pressure-sensitive adhesive, for example, an acrylic adhesive. Typical liquids for use as such volatile solvents, as distinct from emulsion (typically aqueous) polymerization, either singularly or in combination with other volatile and non-volatile solvents, are volatile polar and non-polar organic liquids such as lower molecular weight alkanols (e.g., isopropanol and ethanol), aromatics such as benzene derivatives (e.g., xylene and toluene), lower molecular weight alkanes and cycloalkanes (e.g., hexane, heptane and cyclohexane) and alkanoic acid ester such as ethyl or butyl acetate.

Preferably, the mixture is cast at ambient temperature and pressure followed by evaporation of any volatile solvents, for example, by evaporation at slightly elevated temperatures, to form the matrix. The non-volatile or higher boiling point solvents such as the polyols used in the dermal composition remain therein.

An individual unit or device (often referred to as a "delivery system") comprising the present invention can be prepared in any manner known to those of skill in the art. An exemplary general method of preparation is as follows:

1. Appropriate amounts of the polymers, drugs and/or pressure-sensitive adhesive(s), solvent(s), co-solvent(s), enhancer(s), additive(s) and excipient(s) are combined and thoroughly and uniformly mixed together in a vessel.

2. The matrix is then transferred to a coating operation where it is coated onto a release liner at a controlled specified thickness. The coated composition is then passed through an oven in order to drive off all volatile processing solvents.

3. The composition coated on the release liner is then brought into contact with a backing (layer) and wound into rolls.

4. Appropriate size and shape delivery systems are prepared from the roll material and then pouched.

The order of steps, the amount of the ingredients, and the amount and time of agitation or mixing may be important process variables which will depend on the specific polymers, active agents, solvents or co-solvents, enhancers and additives and excipients used in the composition. These factors can be adjusted by those skilled in the art, while keeping in mind the objects of achieving a solubilized active agent and providing a uniform product. It is believed that a number of other methods, for example, other methods of coating backings that are well-known in the art such as Mayer rod, gravure, knife-over roll, extrusion, casting, calendaring and molding, or changing the order of certain steps, can be carried out and will also give desirable results.

The backing layer, typically occlusive to water permeation, serves to retain and maintain the bioadhesive composition disposed thereon in a defined size and shape, prevent loss of the active agent and/or enhancers to the environment, render the individual unit or delivery system (in conjunction with the release liner) transportable, and generally provide protection both prior to and after application of the unit or system to a subject.

Suitable materials that can be used, singularly, in combination, as laminates or as coextrusions, to form the backing layer are well known in the art and include films or sheets of polyethylene, polyester, polypropylene, polyurethane, polyolefin, polyvinyl alcohol, polyvinyl chloride, polyvinylidene, polyamide, vinyl acetate resins, BAREX®, ethylene/vinyl acetate copolymers, ethylene/ethylacrylate copolymers, metal-vapor deposited films or sheets thereof, rubber sheets or films, expanded synthetic resin sheets or films, non-woven fabrics, fabrics, knitted fabrics, clothes, foils and papers.

The backing layer generally has a thickness in the range of 2 to 1000 micrometers and the matrix is generally disposed on the backing layer in a thickness ranging from about 12 to 250 micrometers. The backing layer may be pigmented, for example colored to either match with or conversely easily distinguish from the site of application, and/or contain printing, labeling and other means of identification and/or traceability of the unit or system itself. The backing layer may further be made opaque or substantially opaque (i.e., preventing light or certain energy wavelengths from penetrating or passing through), such as by metallization, fillers, inks, dyes and the like, for purposes of protecting photosensitive active agents, such as ketoprofen, from degradation and/or preventing photoallergic reactions or irritations on the subject.

The release liner or peel strip is also intended to prevent loss of the active agent and/or enhancers to the environment, and render the individual unit or delivery system (in conjunction with the backing layer) transportable, as well as generally protect the dermal composition from contamination and the like until its application to a subject. The release liner is typically also impermeable and occlusive, and must be compatible with the particular polymers or active agents so as not to interfere with the composition's ultimate application and therapeutic effect.

Suitable materials that can be used, singularly, in combination, as laminates or as coextrusions, to form the release liner are also well known in the art and include any material suitable for the backing layer. When the release liner is composed of a material which typically does not readily release (i.e., is not easily removed or separated from the bioadhesive composition), for example paper, a coating material such as a silicone may be applied to the release liner by any conventional means. Preferred release liners are films commercially available from DuPont, Wilmington, Del., under the trademark Mylar®, and fluropolymer (silicone) coated films commercially available from Rexam Release, Oak Brook, Ill. under the trademark FL2000® and MRL2000®, and from 3M Corporation, St. Paul, Minn. under the trademark Scotch-Pak® 1012 or 1022.

The configuration of an individual unit or delivery system of the present invention can be in any shape, preferably a defined geometric shape, and size (i.e., surface area of application) as is necessary or desirable. The shape is achieved by conventional techniques, for example, cutting or punching, and such techniques are described, for example, in U.S. Pat. Nos. 5,032,207, 5,405,486 and 5,656,285. The intended site of application is an important factor in determining the size and shape of an individual unit or delivery system of the present invention, and can be adjusted by those skilled in the art as is necessary to effect therapy. Typically the size should not exceed 100 cm². Preferred sizes range from about 0.1 cm² to about 60 cm², and more preferred range from about 1.5 cm² to about 30 cm², and optimally from about 2.0 cm² to about 10 cm².

The dermal compositions of the present invention preferably comprise the active agents solubilized therein, and attach directly to the skin after removal of the release liner.

Alternatively, the dermal composition may be a multi-layer delivery system that includes an adhesive layer which attaches directly to the skin after removal of the release liner, and wherein the active agent is initially solubilized or contained in one or more other layers, and which other layers may or may not comprise embodiments of the polymer compositions of the present invention.

In yet another aspect, the dermal composition of the present invention may be a reservoir-type delivery system which is attached to the skin by means of peripheral or intermittent adhesive layers or strips, and wherein the active agent is solubilized or contained in one or more separate matrix reservoir or depot areas. The peripheral or intermittent adhesive layers or strips may or may not comprise embodiments of the polymer compositions of the present invention.

EXAMPLES

In Examples 1-4 and Comparative Example 1, the effect of acrylic functionality on haloperidol flux is determined. Haloperidol and other non-polymer components of a dermal delivery system are formulated in the indicated order to provide a masterbatch.

| Masterbatch (all amounts are in grams) | |
| --- | --- |
| 1. toluene | 17.55 |
| 2. ethanol | 17.80 |
| 3. oleic acid | 1.50 |
| 4. dipropylene glycol | 2.51 |
| 5. Brij 52 | 2.04 |
| 6. haloperidol | 5.00 |
| Total | 46.40 grams. |

To the masterbatch the following acrylic-based polymers are added in the amounts indicated (all amounts are in grams of solution, i.e., solids and solvents):
DT 87-2196 (carboxy functional acrylic PSA, 45% solids) produced by National Starch, Inc.
HRJ 4483 (non-functional acrylic PSA, 50% solids)—produced by Schenectady, International, Inc.

TABLE 1

| Component (grams) | Comp. Ex. 1 | Ex. 1 | Ex. 2 | Ex. 3 | Ex. 4 |
| --- | --- | --- | --- | --- | --- |
| Masterbatch | 4.63 | 4.63 | 4.63 | 4.65 | 4.64 |
| DT 87-2196 | 7.92 | 6.88 | 5.87 | 4.9 | 3.85 |
| HRJ 4483 | — | 1.05 | 2.05 | 2.98 | 4.01 |

The blends are drawn down to 20 mil thickness on a silicone coated release liner using a Gardner fixed gap applicator. The coated release liner is dried at 5 minutes at room temperature and 5 minutes at 85° C. in a convection oven. The coated release liner is then laminated to a 3M 1012 backing layer.

The effect of the acrylic functionality on cumulative haloperidol flux is shown in FIG. 1. For the purposes of this graph, only Examples 2 and 4 and Comparative Example 1 are plotted. As the graph clearly indicates, increasing the amount of non-functional acrylic in the dermal composition, reduces the solubility of the haloperidol resulting in a greater thermodynamic driving force. As a result of the increased thermodynamic driving force, the flux of the haloperidol across the skin increases.

In Examples 5-8 and Comparative Example 2, the effect of acrylic functionality on nicotine flux was determined. Nicotine was combined with the following acrylic polymers in the order and amounts shown. All amounts are shown in grams:
Duro-Tak 87-2852 (carboxy functional acrylic PSA, 34% solids)—produced by National Starch, Inc.
Duro-Tak 87-2097 (non-functional acrylic PSA, 42.5% solids)—produced National Starch, Inc.
HRJ 4483 (see Examples 1-4).

TABLE 2

| Component (grams) | Comp. Ex. 2 | Ex. 5 | Ex. 6 | Ex. 7 | Ex. 8 |
| --- | --- | --- | --- | --- | --- |
| DT 87-2852 | 13.99 | 10.25 | 6.63 | 2.93 | 6.64 |
| DT 87-2097 | — | — | — | — | 6.31 |
| HRJ 4483 | — | 2.51 | 5.01 | 7.53 | — |
| Nicotine | 0.25 | 0.25 | 0.25 | 0.25 | 0.26 |

The blends were prepared according to Examples 1-4, except that the coated release liner was dried in a convection oven at 50° C. for 5 minutes. The effect of the acrylic functionality on nicotine flux is shown in FIG. 2. For purposes of this graph, only Examples 5-7 and Comparative Example 2 were plotted. As the graph indicates, increasing the amount of a non-functional acrylic results in a increasing flux.

In Examples 9-14 and Comparative Example 3, the effect of acrylic functionality on clonidine flux was determined. Clonidine was combined with the following acrylic polymers in the order and amounts shown. All amounts are shown in grams:
Duro-Tak 87-2852 (carboxy functional acrylic PSA, 34 wt % solids)—produced by National Starch, Inc.
Duro-Tak 87-2287 (hydroxy functional vinyl acetate acrylic PSA, 32 wt % solids)

TABLE 3

| Component (grams) | Comp. Ex. 3 | Ex. 9 | Ex. 10 | Ex. 11 | Ex. 12 | Ex. 13 | Ex. 14 |
| --- | --- | --- | --- | --- | --- | --- | --- |
| DT 87-2852 | 14.53 | 11.76 | 8.82 | 5.88 | 2.94 | 1.47 | — |
| DT 87-2287 | — | 2.00 | 5.13 | 8.25 | 11.38 | 12.94 | 14.53 |
| Clonidine Base | 0.36 | 0.36 | 0.36 | 0.36 | 0.36 | 0.36 | 0.36 |

The blends were drawn down to 15 mil thickness on a silicone coated release liner using a Gardner fixed gap applicator. The coated release liner was dried at 5 minutes at room temperature and 5 minutes at 85° C. in a convection oven. The coated release liner was then laminated to a 3M 1012 backing layer. The effect of different acrylic functionality on clonidine flux is shown in FIG. 3. For clarity purposes, only Examples 9-11 and Comparative Example 3 were plotted. As FIG. 3 clearly indicates, increasing the amount of hydroxy functional acrylic in which clonidine has a lower solubility, increases the flux of the clonidine.

In Examples 15-20, the effect of acrylic functionality on scopolamine flux was determined. 0.6 grams of scopolamine, 0.3 grams of oleic acid and 0.2 grams of dipropylene glycol were combined with the following acrylic polymers in the order and amounts shown. All amounts are shown in grams:
Duro-Tak 87-2852 (carboxy functional acrylic PSA, 34 wt % solids)—produced by National Starch, Inc.
Duro-Tak 87-2097 (non-functional acrylic PSA, 42.5% solids)—produced National Starch, Inc.
Duro-Tak 87-2296 (carboxy functional, crosslinked acrylic PSA, 45 wt % solids)—produced by National Starch, Inc.

TABLE 4

| Component (grams) | Ex. 15 | Ex. 16 | Ex. 17 | Ex. 18 | Ex. 19 | Ex. 20 |
| --- | --- | --- | --- | --- | --- | --- |
| DT 87-2852 | — | — | — | 3.09 | 6.18 | 9.26 |
| DT 87-2097 | 7.88 | 5.25 | 2.63 | 7.88 | 5.25 | 2.63 |
| DT 87-2296 | 2.33 | 4.67 | 7.0 | — | — | — |
| Scopolamine Base | 0.6 | 0.6 | 0.6 | 0.6 | 0.6 | 0.6 |
| Oleic Acid | 0.3 | 0.3 | 0.3 | 0.3 | 0.3 | 0.3 |
| Dipropylene glycol | 0.2 | 0.2 | 0.2 | 0.2 | 0.2 | 0.2 |

The blends were drawn down to 15 mil thickness on a silicone coated release liner using a Gardner fixed gap applicator. The coated release liner was dried at 5 minutes at room temperature and 5 minutes at 85° C. in a convection oven. The coated release liner was then laminated to a 3M 1012® or a Dow Chemical Saranexe 2050 backing layer. The effect of different acrylic functionality on scopolamine flux is shown in FIG. 4, along with a commercially available product Transderm Scopolamine™ available from Ciba Geigy, Inc. FIG. 4 clearly indicates that increasing the amount of carboxy functional acrylic decreases the flux of the scopolamine. FIG. 4 also shows the effect that a crosslinked versus non-crosslinked acrylic has on solubility and flux of a drug.

Other embodiments of the invention will be apparent to those skilled in the art from consideration of the specification and practice of the invention disclosed herein. It is intended that the specification be considered as exemplary only, with the true scope and spirit of the invention being indicated by the following claims.

What is claimed is:

1. A method of controlling the flux of a drug from a dermal drug delivery composition, comprising:
    forming a dermal drug delivery composition comprising a polymer matrix and one or more drugs, wherein the polymer matrix comprises at least two polymers including:
        (i) a first acrylic-based adhesive polymer having substantially no functional groups and a first solubility parameter; and
        (ii) a second acrylic-based adhesive polymer having functional groups and a second solubility parameter different from the first solubility parameter, wherein the functional groups are selected from the group consisting of carboxyl groups, hydroxy groups, amido groups and epoxy groups;
    wherein at least one of the one or more drugs has a flux from the composition that is different than the flux of the drug from a corresponding composition comprising a polymer matrix that comprises one of said first or second acrylic-based adhesive polymers, but not both.

2. The method as claimed in claim 1, wherein the first acrylic-based adhesive polymer exhibits a lower solubility for at least one of the one or more drugs than the second acrylic-based adhesive polymer.

3. The method as claimed in claim 2, wherein the first acrylic-based adhesive polymer is present in an amount to achieve a flux of at least one of the one or more drugs which is greater than the flux of the drug from a corresponding composition comprising a polymer matrix that comprises the second acrylic-based adhesive polymer, but not the first acrylic-based adhesive polymer.

4. The method as claimed in claim 2, wherein the amount of the second acrylic-based adhesive polymer is in the range of 5-95 weight % and the amount of the first acrylic-based adhesive polymer is in the range of 95 to 5% by weight, all based on the total dry weight of the first and second acrylic-based adhesive polymers.

5. The method as claimed in claim 2, wherein the amount of the second acrylic-based adhesive polymer is in the range of 20-75 weight % and the amount of the first acrylic-based adhesive polymer is in the range of 75 to 20% by weight, all based on the total dry weight of the first and second acrylic-based adhesive polymers.

6. The method as claimed in claim 1, wherein the second acrylic-based adhesive polymer has carboxyl and/or hydroxyl functional groups.

7. The method as claimed in claim 1, wherein the second acrylic-based adhesive polymer is present in an amount to provide a predetermined saturation concentration of at least one of the one or more drugs in the dermal drug delivery composition.

8. The method as claimed in claim 1, wherein the first acrylic-based adhesive polymer is produced from monomers of alkyl acrylic esters.

9. The method as claimed in claim 1, wherein the functional monomers are incorporated into the second acrylic-based adhesive polymer in an amount of from 4 to 8% by weight, based on the dry weight of the second acrylic-based adhesive polymer.

10. The method as claimed in claim 1, wherein the polymer matrix contains substantially only the first and second acrylic-based adhesive polymers.

11. The method as claimed in claim 1, wherein the second acrylic-based adhesive polymer includes carboxyl functional groups.

12. The method as claimed in claim 11, wherein the one or more drugs includes haloperidol or clonidine.

13. The method as claimed in claim 12, wherein the second acrylic-based adhesive polymer includes 0.1 to 8% by weight of carboxyl functional monomer units, based on the dry weight of the second acrylic-based adhesive polymer.

14. The method as claimed in claim 13, wherein the second acrylic-based adhesive polymer is a crosslinked vinyl acetate acrylic-based adhesive polymer.

15. The method as claimed in claim 11, wherein the one or more drugs includes nicotine.

16. The method as claimed in claim 15, wherein the second acrylic-based adhesive polymer includes 0.1 to 8% by weight of carboxyl functional monomer units, based on the dry weight of the second acrylic-based adhesive polymer.

17. The method as claimed in claim 15, wherein the carboxyl functional monomer units are acrylic acid.

18. The method as claimed in claim 1, wherein the one or more drugs includes scopolamine.

19. The method as claimed in claim 18, wherein the second acrylic-based adhesive polymer includes carboxyl groups.

20. The method as claimed in claim 1, wherein the one or more drugs includes dextramphetamine.

21. The method of claim 1, wherein the one or more drugs includes nicotine.

22. A method as claimed in claim 1, wherein the first and second acrylic-based adhesive polymer are independently selected from homopolymers, copolymers and terpolymers of acrylic acids.

23. A method as claimed in claim 1, wherein the first acrylic-based adhesive polymer is produced from monomers of alkyl acrylic esters or methacrylic esters.

24. A method as claimed in claim 1, wherein the polymer matrix has a net solubility for at least one of the one or more drugs that is proportional to the weight ratio of the first and second acrylic-based adhesive polymers.

* * * * *